United States Patent [19]

Shibata et al.

[11] 4,080,261

[45] Mar. 21, 1978

[54] NOVEL ENDONUCLEASE AND PROCESS FOR PRODUCTION THEREOF

[75] Inventors: Takehiko Shibata, Wako; Tadahiko Ando, Tokyo, both of Japan

[73] Assignee: Rikagaku Kenkyusho, Japan

[21] Appl. No.: 729,969

[22] Filed: Oct. 6, 1976

[30] Foreign Application Priority Data

Oct. 8, 1975    Japan .............................. 50-121671

[51] Int. Cl.² .................. C12D 13/10; C12D 13/06
[52] U.S. Cl. ................................. 195/62; 195/65; 195/66 R; 195/28 N
[58] Field of Search ............... 195/62, 65, 66 R, 28 N

[56] References Cited

U.S. PATENT DOCUMENTS 3,956,064    5/1976    Horikoshi et al. ............... 195/28 N Primary Examiner—Lionel M. Shapiro
Attorney, Agent, or Firm—Bucknam and Archer

[57] ABSTRACT

The present invention relates to new enzymes which decompose nucleic acid and are endowed with a substrate specificity recognizing specific biological desoxyribonucleic acid and cleaving specific bonds thereof to produce fragments of desoxyribonucleic acid of specific sizes and which are obtained by culturing microorganisms belonging to genus Bucillus and purifying the cell free extract thereof by such treatment as streptomycin treatment, ammonium sulfate precipitation, ion exchange chromatography, gel filtration or combination of these processes.

6 Claims, 1 Drawing Figure

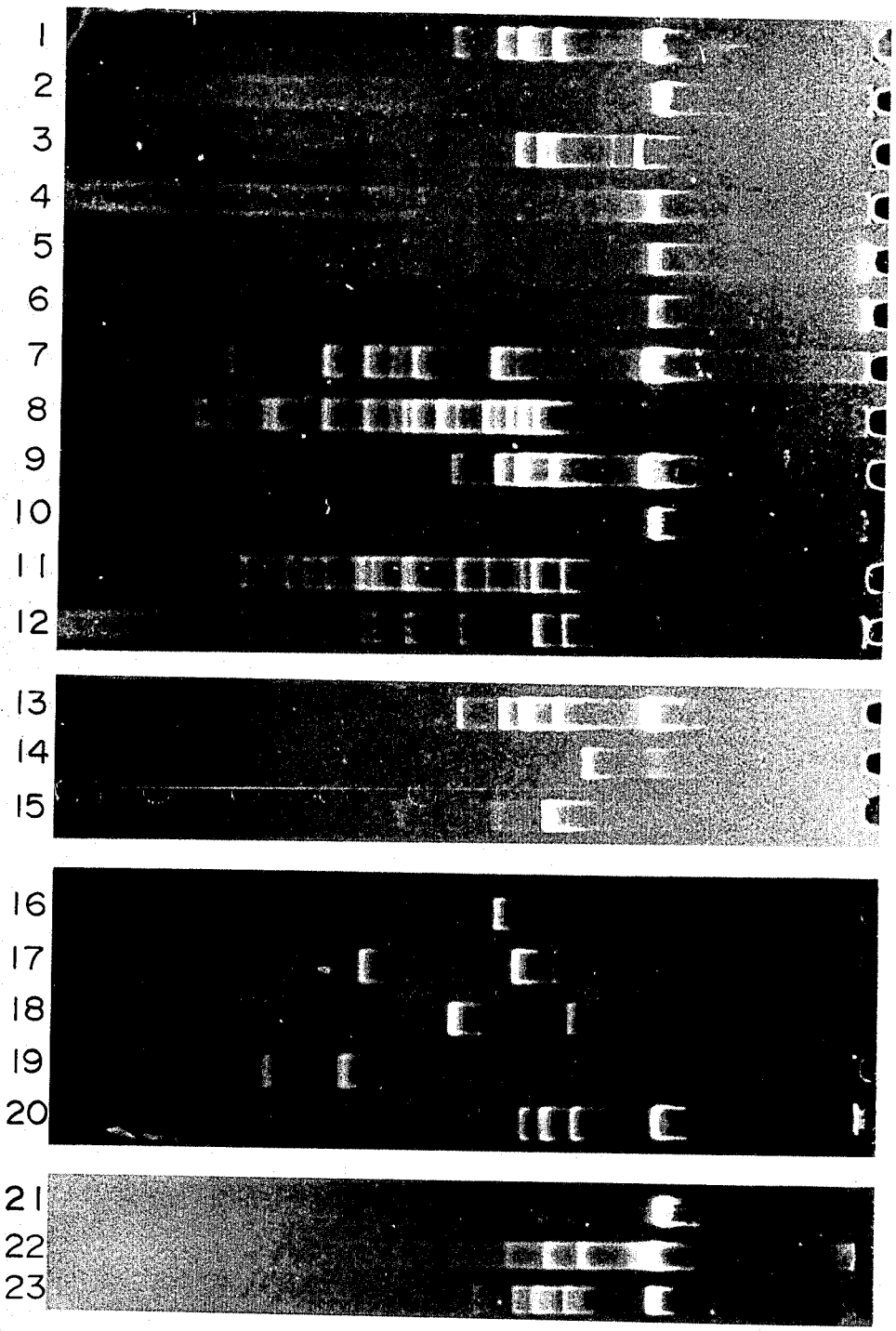

NOVEL ENDONUCLEASE AND PROCESS FOR PRODUCTION THEREOF

FIELD OF THE INVENTION

The present invention relates to new enzymes which decompose nucleic acid and are endowed with a substrate specificity recognizing specific biological desoxyribonucleic acid and cleaving specific bonds thereof to produce fragments of desoxyribonucleic acid of specific sizes and to a process for production thereof.

Enzymes (DNase) which decompose desoxyribonucleic acid (DNA) exist in various biological materials, participate in the important processes of the life phenomena such as metabolism, decomposition, synthesis, substitution of DNA, and have recently drawn particular attention because of their enzymatic chemical characteristics and biological functions. On the other hand, in order to study the structure and function of DNA of the gene, these enzyme have become a powerful means in the production and separation of enzymes having specific action, in the application and development as a biochemical reagent, and in the molecular cloning the gene.

DNA decomposing enzymes are roughly classified into exonuclease and endonuclease according to their function, the former type acting from the end of the polynucleotide chain of the molecule of DNA and successively liberating and decomposing nucleotide, the latter type forming fragment of DNA or oligonucleotide by cleaving the phosphodiester bond in the DNA molecule.

DESCRIPTION OF THE PRIOR ART

Recently, in the study of endonuclease type enzymes, great progress has been achieved in the studies on enzymes which show a specificity of the structure of DNA, particularly to the configuration of nucleotide or to the structural change which exists in nature or is introduced artificially, on enzymes which act by recognizing a specific biological DNA, and on enzymes which have biologically important function (refer to Tadahiko Ando: Chemistry and Life, Vol. 13, No. 6, p. 342).

The present inventors performed the following studies and established methods of production of each enzyme. By a series of studies the present inventors accomplished methods for producing enzymes, more particularly a method for producing enzymes from the culture of Aspergilus oryzae, which do not act upon double-stranded DNA and specifically decompose single-stranded DNA. (Japanese Pat. No. 593,368); a method of producing enzymes from the fungus of Aspergilus oryzae which preferentially decompose purine-purin bond (Japanese Pat. No. 621,205); a method of producing enzymes which introduce a limited number of single-strand breaks in duplex DNA obtained from Escherichia coli infected with bacteriophage (Japanese Pat. No. 764,919); a method of producing an enzyme which hydrolyzes RNA to nucleoside-2,3-cyclic phosphate obtained from Escherichia coli infected or induced by bacteriophage (Japanese patent application 78869/1972, Japanese patent disclosure 35577/1074); a method of producing enzymes which preferentially cleave guanine-guanine bond in the molecule of DNA, from the culture liquid of alkalophilic bacteria microbes (Japanese patent application 114131/1973, Japanese patent disclosure 64484/1975); and a method of producing enzyme which specifically decompose RNA moiety of DNA-RNA hybrid obtained from the cells of Bacillus subtilis (Japanese patent application 127276/1974).

SUMMARY OF THE INVENTION

Heretofore, studies have centered on the phenomena that the host-range of phage is controlled by host and on host controlled modification and restriction and it has been found that there is a mechanism whereby Escherichia coli modifies λ phage DNA and controls unmodified foreign DNA.

While eagerly studying new enzymes which decompose DNA produced by various microorganisms, the inventors have succeeded in collecting new enzymes which decompose DNA and are endowed with a specificity to segment at specific positions in the molecule of DNA by recognizing DNA of a specific biomicrobe obtained from the cells of aerobic bacillus with spore belonging to genus Bacillus such as *Bacillus amyloliquefaciens, Bacillus subtilis,* and to form fragment of DNA of specific size, and have completed this invention.

Therefore the object of the present invention is to provide an enzyme having the specific biological activity above mentioned.

Another object of the present invention is to provide a process for producing said enzymes.

BRIEF DESCRIPTION OF THE DRAWING

The drawing is a photograph showing the results of agarose gel electrophoresis of DNA treated by the present enzymes, Endo. R. Bam NI, Endo. R. Bam NII, and Endo. R. Bam NIII.

The numerals in the drawing have the following meanings.

1 — phage λ DNA treated with Endo. R. EcoRl (control)
2 — untreated phage λ DNA
3 — phage λ DNA treated with Endo. R. Bam NI
4 — λ·H I treated with Endo. R. Bam NI
5 — untreated phage φ105C·168DNA (control)
6 — phage φ105C·N DNA treated with Endo. R. Bam NII, NIII
7 — phage φ105C·H DNA (which cannot be cleaved by Endo. R. Bam NII) treated with Endo. R. Bam NII, NIII
8 — phage φ105C·168 DNA treated with Endo. R. Bam NII, NIII
9 — phage λ DNA treated with Endo. R. Eco Rl (control)
10 — untreated phage λ DNA
11, 12 — phage λ DNA treated with Endo. R. Bam NII, NIII
13 — phage λ DNA treated with Endo. R. Eco Rl (control)
14 — untreated λ dv 1 DNA
15 — λ dvi DNA treated with Endo. R. Bam NII, NIII
16 — untreated Col EI DNA
17 — Col EI DNA treated with Endo. R. Bam NII, NIII
18 — untreated SV40 DNA
19 — SV40 DNA treated with Endo. R. Bam NII, NIII
20 — phage λ DNA treated with Endo. R. Eco Rl (control)
21 — untreated phage SPPI·168 DNA 22 — phage SPPI·168 DNA treated with Endo. R. Bam NII, NIII 23 — phage λ DNA treated with Endo. R. Eco Rl (control)

DESCRIPTION OF THE PREFERRED EMBODIMENTS

It is a characteristic of the present enzymes that they are capable of recognizing specific nucleic acids and selectively cleaving the phosphodiester bond in the nucleic acids to produce nucleic acid fragments having discrete molecular weight, and the enzymes are obtained from a cell free extract of the species belonging to genus Bacillus.

The microorganisms used to obtain the present enzymes belong to Genus Bacillus, and any of the strains belonging to genus Bacillus and having an ability to produce the present enzyme can be used in this invention, for example *Bacillus subtilis* which was deposited in unristricted form with the Institute of Applied Microbiology, University of Tokyo (Address: 1—1, Yayoi, Bunkyoku, Tokyo, Japan) as IAM 1522 (see JPCC Catalogue of Culture, page 41, 1966), this microorganism being freely available to any third party at any time. On the other hand, the species of *Bacillus amyloliquefaciens* had been assigned the American Type Culture Collection (ATCC) (12301 Parklawn Drive Rockville, Md. 20852) as ATCC access number 23,845, and is on deposit with ATCC in an unrestricted deposit permitting the public full access to the culture. The species was released for distribution to the public on Sept. 8, 1976.

The applicant will maintain the deposition of IAM 1522 and ATCC 23,845 in the unristricted form until the end of the duration of a patent granted on this application if a patent is granted on this application, and thus the microorganism IAM 1522 and ATCC 23,845 strains will be available to any third party at any time until the end of the duration of the patent granted on this application.

The said microorganisms can be cultured by following a general culture method, for example, by inoculating the above-mentioned microorganism in a culture medium containing amino acid, casein decomposition product, glucose, phosphate, sulfate, etc., and culturing it at about 30° – 37° C with aeration and agitation.

A typical culture medium is illustrated below.

| (1) CI medium | in 10 liter |
|---|---|
| $KH_2PO_4$ | 60 g |
| $K_2HPO_4$ | 140 g |
| Na citrate . $2H_2O$ | 10 g |
| $(NH_4)_2SO_4$ | 20 g |
| Arginine | 2 g |
| Casamino acid | 2 g |
| Glucose | 50 g |
| $MgSO_4$ | 2 g |
| Tryptophan | 0.25 g |
| (2) Bacto-Penassay broth (Difco) | |

The growth of the microorganism is measured by placing the culture broth in a crevette and measuring transmittance thereof using light of a wavelength of 660 m μ.

In the present invention the cells are collected, preferably at the time of their logarithmic phase and at the beginning of their stationary phase and the cells themselves or the protoplast obtained by treating cells with lysozyme are crushed with supersonic waves, and a cell-free extract is obtained by centrifugal separation. The obtained cell-free extract is treated with streptomycin sulfate and precipitation treatment with ammonium sulfate, subjected to gel filtration method using ultragel ACA 44 or Cefadex G-100, subjected to ion exchange chromatography method using DEAE-Cellulose, phosphocellulose, or treated by a combination of these methods, and as a result three kinds of new endonuclease type enzymes which decompose DNA are collected from the cells (said enzymes hereafter being referred to as "Endo. R. Bam NI", "Endo. R. Bam NII" and "Endo. R. Bam NIII".

Accordingly, enzymes of this invention can be prepared by subjecting the cell-free extract obtained from the cultured microorganism during its logarithmic phase and stationary phase to streptomycin treatment, ammonium sulfate precipitation, ion exchange chromatography method, gel filtration method, or combination of these methods.

The most active enzymes can be obtained using the microorganisms collected at the time of logarithmic phase and at the beginning of stationary phase.

The enzymes obtained in this manner have been proved to have the following physicochemical characteristics.

Physicochemical Characteristics of the Enzymes:

(1) Activity and Substrate Specificity:

DNA of each of the following phages was prepared and used: as a substrate DNA of enzymatic reaction, Bacillus phage φ 105 (φ 105 C.N), carrying modification type of Bacillus subtilis (IAM 1522); φ 105 C (φ 105 C.H) carrying modification type of *Bacillus subtilis* (IAM 1521) (which is presently called as *Bacillus amyloliquefaciens* H strain); Bacillus phage φ 105 C (φ 105 C. 168) carrying modification type of *Bacillus subtilis* Marburg 168; φ 29 grown on *Bacillus subtilis* 168 (ATCC 6051) or *Bacillus amyloliquefaciens* H; $M_2$ grown on *Bacillus subtilis* 168 (ATCC 6051); φ $NR_2$ grown on *Bacillus megaterium* 203; coliphage T7 grown on *Escherichia coli* B; and coliphage λ grown on *Escherichia coli* $K_{12}$ strain; φ 105, 168 being Bacillus phage φ 105 C, grown on *Bacillus subtilis* ATCC 6051; SPPI·168 being Bacillus phage SPPI, grown on *Bacillus subtilis* ATCC 6051; φ 105C·N being Bacillus phage φ 105C, grown on *Bacillus subtilis* IAM 1522; φ 105C·H being Bacillus phage 105C, grown on *Bacillus amyloliquefaciens* H strain; λ HI being λDNA, carrying modification type of *Bacillus amyloliquefaciens* HI strain; λ DNA being untreated λDNA, grown on Escherichia coli B strain; Eco Rl being coli phage λDNA treated by Eco Rl enzyme of *Escherichia coli*; λdv I and Col EI being plasmide (cellular intrinsic factor) of *Escherichia coli*; and SV 40 being ternocer Virus Simian Virus 40. The term Endo. R. is abbreviation of Endonuclease R.

After the enzymatic reaction, when the size of the substrate DNA cleaved by agarose gel electrophoresis and the number of the cut positions were examined the electrophoresis figure shown in the drawing was obtained for the treatment by Endo. R. Bam NI, Endo. R. Bam NII and Endo. R. Bam NIII.

The drawing is a photograph showing an agarose gel electrophoresis figure of the substrate DNA treated by Endo. R. Bam NI, Endo. R. Bam NII and Endo. R. Bam NIII. As shown in the drawing the molecure of DNA substrate DNA was segmented into fragments of specific size by Endo. R. Bam NI, Endo. R. Bam NII and Endo. R. Bam NIII. Summarizing these experimental results, it is clear that the above-mentioned three enzymes exhibit substrate specificity as shown in Table 1.

Table 1

| Substrate DNA | Number of cleaved positions | | |
|---|---|---|---|
| | Endo. R. Bam NI | Endo. R. Bam NII | Endo. R. Bam NIII |
| Bacillus phage φ 105 C.N. | 0 | 0 | 0 |
| Bacillus phage φ 105 C-168 | 0 | 16 | — |
| Bacillus phage φ 105 C.H | 0 | 7 | — |
| Bacillus phage φ 29 | 0 | 0 | 0 |
| Bacillus phage $M_2$ | 0 | 0 | 0 |
| Bacillus phage φ $NR_2$ | 0 | — | — |
| Coli phage λ | 5 | about 15 | |
| Coli phage T7 | 0 | about 10–15 | |
| Bacillus phage SPPI | 0 | 3 | |
| λ dv I* | 1 | 2 (or 3) | |
| Col EI* | 0 | 3 | |
| SV 40** | 1 | >4 | |

*λ dv I, Col EI - plasmide (cellular intrinsic factor of *Escherichia coli*)
**SV 40 - tumor virus (Simian Virus 40)

Endo. R. Bam NI did not act upon any DNA of φ 105 C.N, φ 105 H, φ 105–168, φ 29, $M_2$, SPPI, T7, Col E1, but cleave DNA of coli phage λ and the number of the cleaving positions was 5 per molecule of DNA. Endo. R. Bam NI also cleave λ dv DNA and SV 40 DNA at one position respectively.

Endo. R. Bam NII did not act upon DNA of φ 105 C.N and φ 105 C.H, but was found to cleave DNA of φ 105 C.168 at about 7 positions, and to cleave DNA of T7, λ, SPPI, λ dv I at several positions.

And Endo. R. Bam NIII did not act upon DNA of φ 105 C.N but was found to cleave DNA of φ 105 C.168 and φ 105 C.H at about 9 positions and 7 positions respectively, and to cleave DNA of T7, λ, SPPI, λ dv I, Col EI, and SV 40 at several positions to form specific fragments of DNA.

(2) Optimum pH:

All of Endo. R. Bam NI, Endo. R. Bam NII and Endo. R. Bam NIII were found to have their optimum pH range between pH 7.2 – 8.3.

(3) Range of Working Temperature: 20° – 40° C, optimally 35° – 37° C.

(4) Method for Measuring Potency:

The enzymatic activity was measured by adding the enzyme sample to 50 mM Tris-hydrochloric acid buffer (pH 7.5), 5 mM $MgCl_2$, 0.2 mMEDTA, 5 mM β-mercaptoethanol, and 3.3 μg/ml DNA to make 30 μl–300 μl of an enzyme reaction solution and the solution was treated at 37° C for 50 minutes. After the reaction, as no formation of acid soluble nucleotide was observed, the segmentization of the substrate DNA of the reaction products was examined by electrophoresis using agarose gel or neutral sucrose gradient centrifugal method.

(5) Inhibition, Activation and Stabilization:

Endo. R. Bam NI was activated by 0.3 – 10 mM of $Mg^{2+}$, and was inhibited by more than 20 mmM of $Mg^{2+}$ and by more than 0.2 M of NaCl, Endo. R. Bam NII was activated by 10 – 20 M of $Mg^{2+}$, and was inhibited by more than 0.2 M of NaCl. Endo. R. Bam NI, Endo. R. Bam NII and Endo. R. Bam NIII were markedly inhibited by 5 mM of EDTA.

None of Endo. R. Bam NI, Endo. R. Bam NII or Endo. R. Bam NIII required a co-factor such as ATP and S-adenosylmethionine.

(6) Method of Purification:

A method for purifying the present enzymes is shown in the following:

Cell
↓
Lysozyme treatment
↓
Supersonic wave treatment
↓
Streptomycin treatment
↓
Ammonium sulfate precipitation (40 weight % to saturated solution)
↓
Gel filtration (LKB AcA 44)
↓
┌────────────┴────────────┐
Low molecular weight      High molecular weight
↓                         ↓
DEAE-Cellulose chro-      DEAE-Cellulose chromatography
matography                (0.05 to 0.1M NaCl)  (0.12 to 0.25M NaCl)
(0.05 to 0.1M NaCl)
↓                         ↓
Endo R. Bam NI            Endo. R. Bam NII and III
↓                         ↓
Native DNA-Cellulose      Native DNA-Cellulose
chromatography            chromatography
(0.2 to 0.3M NaCl)        (0.35M NaCl)
↓                         ↓
Endo R. Bam NI            Endo. R. Bam NII and III (7) Molecular weight:

Molecular weight of the present enzymes were measured by gel-filtration method.

M.W. of Endo. R. Bam NI: about ten to one hundred thousand

M.W. of Endo. R. Bam NII and III: about one hundred thousand (8) Elementary analysis:

The measurement of an elementary analysis is is not yet performed.

As described above in detail, the enzymes of this invention recognize DNA of specific organisms such as bacillus group strains and bacteriophage, and cleave the bond at their specific positions to form DNA fragments of specific size. The enzymes of this invention are new enzymes decomposing nucleic acid and are endowed with a high substrate specificity not known in any published literature, and the process of this invention is one which efficiently produces the enzymes.

Hereafter, the methods of this invention are illustrated by way of examples. However the examples are illustrated only for the explanation of this invention, and are not intend to restrict the scope of this invention.

1. Example 1

The above-mentioned *Bacillus subtilis* (IAM 1522) was pre-cultured in 500 ml of a brain-heart-infusion-medium, at 30° C for 13 – 15 hours under aeration and agitation, and this pre-culture solution was suspended in 20 l of the culture medium having the following formulation.

| | | | |
|---|---|---|---|
| K$_2$HPO$_4$ | 120 g | Arginine chloride | 4 g |
| KH$_2$PO$_4$ | 280 g | glucose | 100 g |
| sodium citrate | 20 g | MgSO$_4$ | 4 g |
| ammonium sulfate | 40 g | Tryptophan | 0.5 g |
| Casamino acid (vitamine-free) | 4 g | | |

After culturing at 35° C for 4 – 6 hours under aeration and agitation, the cultured cells at the early stationary phase stage were collected. When this culture broth was centrifuged by continuous freeze centrifugal method, about 32 g of the cells were obtained.

The cells were suspended in 1 L of PES buffer (which contained 0.12 M potassium phosphate buffer: pH 7.2, MgCl$_2$ 5 mM, EDTA 0.1 mM, cane sugar 171 g), to which 0.3 g of egg-white lysozyme was added and allowed to stand at 37° C for 30 – 60 minutes and a ball shaped protoplast was obtained. About 16 g of the protoplast was collected by centrifuge, and after freezing by liquid nitrogen or dry ice-acton, it was stored in an extra low temperature bath of −80° C.

4 g of protoplast was suspended in 15 ml of 50 mM Tris-hydrochloric acid buffer (pH 7.5) which contained 0.1 mM EDTA, 5 mM MgCl$_2$, 2 mM β-mercaptoethanol, the protoplast were crushed by supersonic wave treatment (20 KC, 30 seconds, 3 times), and the crushed mass was treated by freeze centrifuge at 80,000 g for 60 minutes. To the centrifuged supernatant liquid was added under agitation a streptomycin sulfate solution to make 1% solution. After further agitating for 10 minutes, the supernatant liquid was separated by centrifugation at low temperature (0° – 5° C). To this supernatant liquid, ammonium sulfate was added over 30 minutes to make a 40% saturated solution which was subjected to further agitation for 15 minutes. The formed precipitates were removed by centrifugation at low temperature. To the obtained supernatant liquid, ammonium sulfate was added with agitation over 30 minutes to make a 60% saturated solution, which was further agitated for 15 minutes. Then the formed precipitates were collected by a refrigerated centrifuge, suspended and dissolved in 3 ml of Tris-hydrochloric buffer solution pH 7.5 (D8) which contained 0.1 mM EDTA, 2 mM MgCl$_2$, 2 mM β mercaptoethanol. (Ammonium sulfate fraction).

In this fraction, three active DNA decomposing enzymes, namely, Endo. R. Bam NI, Endo. R. Bam NII and Endo. R. Bam NIII were contained.

EXAMPLE 2

(Purification Method 1)

After the ammonium sulfate fraction was dialyzed by D8 buffer solution mentioned in Example 1, it was absorbed in a DEAE-cellulose column (15 × 200 mm) previously washed with D8 buffer solution. By eluting under linear gradient of 0 – 0.4 M sodium chloride concentration by the same buffer solution, Endo. R. Bam NI was eluted in the fraction of 0.05 – 0.1 sodium chloride concentration, and Endo. R. Bam NII and Endo. R. Bam NIII were eluted in the fraction of 0.09 – 0.2 M.

EXAMPLE 3

(Purification Method 2)

After the ammonium sulfate fraction obtained in example 1 was dialyzed by D8 buffer solution, it was absorbed in a phosphocellulose P11 Column (15 × 200 mm) previously washed with the same buffer solution. By eluting under a linear gradient of 0 – 0.7 sodium chloride concentration by the same buffer solution, Endo. R. Bam NI active component, was eluted over a wide range.

And Endo. R. Bam NII and Endo. R. Bam NIII active components were eluted in the 0.3 – 0.5 M sodium chloride fraction.

EXAMPLE 4

(Purification Method 3)

When the ammonium sulfate fraction obtained in Example 1 was eluted by D8 buffer solution by gel filtration method using an ultra gel ACA-44 column (20 × 400 mm), Endo. R. Bam NII and Endo. R. Bam NIII active moiety were eluted in advance, and after passing through of 1.5 – 2 times the column volume of eluting solution, Endo. R. Bam NI action moiety were separately eluted (Gel filtration eluate fraction).

EXAMPLE 5

(Purification Method 4)

A combination method of separating and purificating methods 1, 2 and 3 shown in Example 2, 3 and 4 respectively is shown hereinafter.

First, when the ammonium sulfate fraction obtained in Example 1 was fractionated by the gel filtration method described in Example 4, Endo. R. Bam NII and Endo. R. Bam NIII appeared in the liquid passed through. These fractions were separated and concentrated by DEAE-Cellulose-chromatography method described in the purification method I, and they were further allowed to be absorbed and eluted by phosphocellulose-column chromatography as described in Example 3 (Purification Method 2).

On the other hand, when the fraction of Endo. R. Bam NI, which is eluted subsequent to the abovementioned gel filtration method, was absorbed by the DEAE-cellulose column chromatography described in Example 2 (purification method 1) and eluted by sodium chloride concentration gradient, and then Endo. R. Bam NI was eluted in the fraction of 0.06 – 0.90 M.

EXAMPLE 6

(Purification Method 5)

By purification according to Purification Method 1 of Endo. R. Bam NI fraction and Endo. R. Bam II and III fraction obtained in Purification Method 3, Endo. R. NI was recovered from Endo. R. Bam NI fraction and Endo. R. Bam II and III from Endo. R. Bam II and III fraction, and Endo. R. Bam NI was further purified according to Purification Method 2 or by Native DNA-cellulose chromatography.

On the other hand, the recovered Endo. R. Bam NII and III fraction which contained a small amount of Endo. R. Bam NI was purified into pure Endo. R. Bam NII and III according to Purification Method 1 eliminating contained Endo. R. Bam NI. The obtained Endo. R. Bam NII and III was further purified by Purification Method 2 or Native DNA-cellulose chromatography method.

What is claimed is:

1. Endonuclease R NI capable of selectively recognizing specific nucleic acids and cleaving the phosphodiester bond in the nucleic acids at at least one nonterminal position to produce nucleic acid fragments having discrete molecular weight, of molecular weight between 10,000 and 100,000 capable of cleaving Coli phage λ in 5 positions, λ dv I DNA and Simian Virus 40 in one position, having an activity of optimum pH range 7.2–8.3, having optimum temperature range at 35°–37° C, activated by 0.3–10 mM of $Mg^{+2}$, inhibited by more than 20 mmM of $Mg^{+2}$ and more than 0.2 M of NaCl, inhibited by 5 mM of EDTA, said enzyme being obtained from a cell-free extract of the species IAM 1522 and ATCC 23,845 of Genus Bacillus in a culture medium, collecting the cells thereof, obtaining cell free extract therefrom, fractionating said extract.

2. Endonuclease R NII capable of selectively recognizing specific nucleic acids and cleaving the phosphodiester bond in the nucleic acids to produce nucleic acid fragments having discrete molecular weight, of molecular weight about 100,000, capable of cleaving Bacillus phage φ 105 C-168 in 16 positions, Coli phage λ in about 15 positions, Coli phage T7 in about 10–15 positions, λ dv I DNA in 2 or 3 positions, Col EI in three positions, Simian virus 40 at more than four positions, activated by 10–20 M of $Mg^{2+}$, inhibited by more than 0.2M of NaCl, inhibited by 5 mM of EDTA, said enzyme being obtained from a cell-free extract of the species IAM 1522 and ATCC 23,845 Bacillus in a culture medium, collecting the cells thereof, obtaining cell free extract therefrom, fractionating said extract.

3. Process for producing endonuclease R Bam NI, R Bam NII and R Bam NIII which comprises cultivating a strain of Species IAM 1522 or ATCC 23,845 of Genus Bacillus in a culture medium, collecting the cells thereof, obtaining cell free extract therefrom, fractionating said extract and purifying the fractionated extract.

4. Process according to claim 3 wherein said endonuclease is Endonuclease R. Bam NI.

5. Process according to claim 3 wherein said endonuclease is Endonuclease R. Bam NII.

6. Process according to claim 3 wherein said endonuclease is Endonuclease R. Bam NIII.

* * * * *